United States Patent [19]

Middleton

[11] Patent Number: 4,621,126

[45] Date of Patent: Nov. 4, 1986

[54] GROUP TRANSFER POLYMERIZATION EMPLOYING TRIS(DISUBSTITUTED AMINO)SULFONIUM PERFLUOROCARBANION SALTS AS CATALYSTS

[75] Inventor: William J. Middleton, Chadds Ford, Pa.

[73] Assignee: E. I. Du Pont de Nemours and Company, Wilmington, Del.

[21] Appl. No.: 731,499

[22] Filed: May 7, 1985

Related U.S. Application Data

[62] Division of Ser. No. 618,737, Jun. 8, 1984, Pat. No. 4,535,184.

[51] Int. Cl.[4] ............................ C08F 4/00; C08F 18/10
[52] U.S. Cl. .................................... 526/192; 526/194; 526/204; 526/217; 526/220; 526/329.7
[58] Field of Search ............... 526/204, 206, 220, 222, 526/329.7, 192, 194

[56] References Cited

U.S. PATENT DOCUMENTS 3,940,402  2/1976  Middleton ..................... 260/293.63
4,524,196  6/1985  Farnham et al. ................... 526/190

OTHER PUBLICATIONS

Chambers et al., J.C.S. Perkin I, 1980, 435–439.
Delyagina et al., Izv. Akad. Nauk SSSR, Ser. Khim., No. 10, 2238–2243 (1981).
Young, Fluorine Chem. Rev., 1967, 1 359–397 particularly pp. 360–366, 371–377 and 383–387.
Brunskill et al., Chem. Communications, 1970, 1444–1446.
Banderman et al., "Group Transfer Polymerization of Methyl Methacrylate", Polym. Preprints, 27(1), 169 (1986).
Webster, O. W. et al., J. Am. Chem. Soc., 105, pp. 5706–5707 (1983).

*Primary Examiner*—Joseph L. Schofer
*Assistant Examiner*—F. M. Teskin

[57] ABSTRACT

Tris(disubstituted amino)sulfonium perfluorocarbanion salts, process for their preparation and the use thereof as catalysts in group transfer polymerization.

7 Claims, No Drawings

GROUP TRANSFER POLYMERIZATION EMPLOYING TRIS(DISUBSTITUTED AMINO)SULFONIUM PERFLUOROCARBANION SALTS AS CATALYSTS

CROSS-REFERENCE TO RELATED APPLICATION

This is a division of application Ser. No. 618,737 filed June 8, 1984 and issued Aug. 13, 1985 as U.S. Pat. No. 4,535,184.

BACKGROUND OF THE INVENTION

1. Field of the Invention

This invention relates to tris(disubstituted amino)sulfonium perfluorocarbanion salts and to process for the preparation thereof, the carbanion salts being useful as polymerization catalysts and as reagents for preparing fluoro-organic compounds.

2. Background

Tris(dialkylamino)sulfonium (TAS) salts of the formula $(R^1R^2N)(R^3R^4N)(R^5R^6N)S^\oplus X^\ominus$ wherein each R is $C_{1-20}$ alkyl having at least two α-hydrogen atoms and X is $(CH_3)_3SiF_2$, Cl, Br, I, CN, NCO, NCS, $NO_2$ or $N_3$ are disclosed in U.S. Pat. No. 3,940,402. The TAS salts are soluble in organic liquids and are useful as polymerization catalysts and as reagents for replacing various groups in organic compounds with the group X.

Chambers et al., J.C.S. Perkin I, 1980, 435–439, disclose the preparation of fluorocarbanions by reacting CsF and selected fluoroolefins in dimethylformamide (DMF), the olefins being perfluorocycloalkene derivatives. The product anions are observed by $^{19}F$ NMR spectroscopy and are trapped with bromine or chlorine to give bromo- or chloro-fluorocycloalkanes.

The preparation of solutions of N,N,N'N'-tetramethylformamidinium perfluorocarbanions in DMF by reacting $[(CH_3)_2N]_2C^\oplus HF_2^\ominus$ and branched perfluoroolefins is disclosed by Delyagina et al., Izv. Akad. Nauk SSSR, Ser. Khim., No. 10, 2238–2243 (1981), English language translation. The carbanions are characterized in solution by $^{19}F$ NMR spectroscopy and found to be stable at low temperature.

Young, Fluorine Chem. Rev., 1967, 1, 359–397, particularly pages 360–336, 371–377 and 383–387, reviews perfluoroalkyl carbanion chemistry, in general, and the dimerization and polymerization of olefins, in particular. The use of fluorocarbanions in nucleophilic displacements, particularly for fluoroalkyl iodide synthesis, is discussed in detail.

Brunskill et al., Chem. Communications, 1970, 1444–1446, disclose the fluoride ion-catalyzed oligomerization (dimerization and trimerization) of hexafluoropropene and the formation of heptafluoroisopropyl carbanion.

DETAILED DESCRIPTION OF THE INVENTION

For further comprehension of the invention, and of the objects and advantages thereof, reference may be made to the following description and to the appended claims in which the various novel features of the invention are more particularly set forth.

The invention resides in tris(disubstituted amino)sulfonium perfluorocarbanion salts of the formula

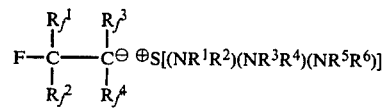

$R^1$ through $R^6$, each selected independently are $C_1-C_{20}$ alkyl, each having at least 2 alpha hydrogen atoms, or any or all of the pairs $R^1$ and $R^2$, $R^3$ and $R^4$, and $R^5$ and $R^6$, each pair selected independently, are $—CH_2—_4$ or $—CH_2—_2CHY—CH_2—_2$, wherein Y is hydrogen or methyl;

$R_f^1$, $R_f^2$ and $R_f^3$, each selected independently, are F, $C_{1-20}$ perfluoroalkyl or $C_{4-12}$ perfluorocycloalkyl; and $R_f^4$ is $C_{1-20}$ perfluoroalkyl or $C_{4-12}$ perfluorocycloalkyl; or any one of the pairs $R_f^1$ and $R_f^2$, $R_f^3$ and $R_f^4$, $R_f^1$ and $R_f^3$, and $R_f^2$ and $R_f^4$, taken together, is $—CF_2—_n$ wherein n is an integer and is 2 to 6; or each of the pairs $R_f^1$ and $R_f^2$ and $R_f^3$ and $R_4^4$, or each of the pairs $R_f^1$ and $R_f^3$ and $R_f^2$ and $R_4^4$, taken together, is $—CF_2—_n$ wherein n, each selected independently, is an integer and is 2 to 6.

The invention also resides in a process for the preparation of the perfluorocarbanion salts. The process comprises contacting and reacting, in an inert solvent, the perfluoroolefin of the formula

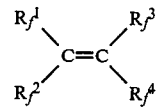

and the sulfonium salt of the formula

All symbols are as defined above.

Suitable solvents include any inert solvent, that is, a solvent that will dissolve the sulfonium salt without reacting with it. Examples include nitriles, such as acetonitrile, propionitrile, and benzonitrile, and amines, such as pyridine and quinoline.

The reaction can be carried out at −100° to 100° C. Higher temperatures can be used, but generally provide no advantage. The preferred temperature range is −80° to 50° C.

Ambient pressure is preferred for the reaction because of convenience, but either subatmospheric pressure or superatmospheric pressure is operable.

The reaction can be carried out with or without a solvent, although the presence of a solvent is preferred. When a solvent is employed, the fluoroolefin and the sulfonium salt should be present in concentrations of at least about 0.001 molar, preferably at least about 0.01 molar, more preferably at least about 0.1 molar. Either reactant can be in moderate excess, but best yields are achieved when the reactants are used in approximately equimolar amounts. A large excess of either reactant may lead to undesirable further reaction of the desired product of the invention. However, in selected instances, such as those demonstrated in Utility Examples N and O, use of excess fluoroolefin to induce further reaction may be desirable.

Either reactant can be added to the solvent first, followed by addition of the second reactant or both reactants can be added to the solvent simultaneously. Alternatively, either or both reactants can be prepared in situ in the solvent, reaction then taking place when both reactants are present.

Many of the carbanion salts can be isolated as crystalline solids by the evaporation of the reaction solvent at reduced pressure. The isolable salts contain tertiary carbanions which are cyclic, or acyclic and devoid of branched α-carbon atoms. Salts which contain secondary carbanions, or certain tertiary acyclic carbanions having branched α-carbon atoms, may not be isolable. Such salts are exemplified in Examples 4–7 (infra). Those of Examples 4 and 5 can be identified in solution, for example, spectroscopically or by $^{19}$F NMR, and used directly in subsequent reactions, as described hereinafter. Salts of Examples 6 and 7 are not readily identifiable in solution, but can be used in subsequent reactions and can be unequivocally identified as intermediates to the products isolated.

Preferred carbanion salts of the invention are those wherein $R_f^1$ is F, $R_f^2$ is F or $C_{1-10}$ perfluoroalkyl, and $R_f^3$ and $R_f^4$ are each $CF_3$. More preferred are the above salts wherein $R^1$–$R^6$ are each $CH_3$ or the pairs $R^1$ and $R^2$, $R^3$ and $R^4$, and $R^5$ and $R^6$ are each —$CH_2$—$_5$. Most preferred salts are those wherein $R_f^1$ is F, $R_f^2$ is F, $CF_3$ or $C_2F_5$, $R_f^3$ and $R_f^4$ are each $CF_3$ and $R^1$–$R^6$ are each $CH_3$.

Preferred fluoroolefins for use in the invention process are those wherein $R_f^1$ is F, $R_f^2$ is F or $C_{1-10}$ perfluoroalkyl, more preferably F, $CF_3$ or $C_2F_5$, and $R_f^3$ and $R_f^4$ are each $CF_3$. Preferred starting sulfonium salts are those wherein $R^1$–$R^6$ are each $CH_3$, or the pairs $R^1$ and $R^2$, $R^3$ and $R^4$, and $R^5$ and $R^6$ are each —$CH_2$—$_5$. Most preferred starting sulfonium salts are those wherein $R^1$–$R^6$ are each $CH_3$.

Examples of perfluorocarbanion salts of the invention, and the reactants that can be used to prepare them, are shown in the following table.

| Reactants | Product |
|---|---|
| 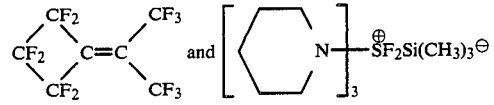 | 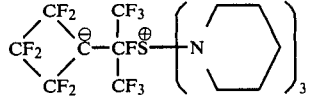 |
| 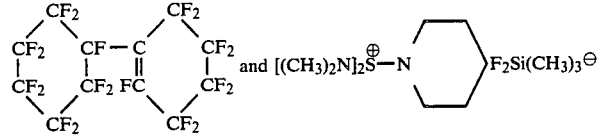 | 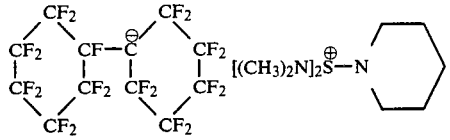 |
| 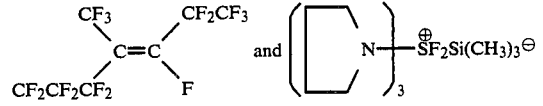 | 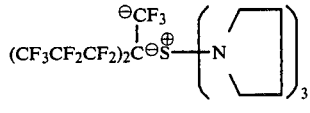 |
| 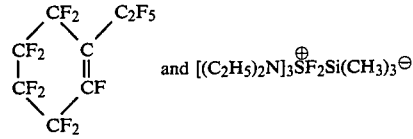 | 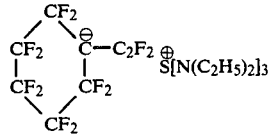 |
| 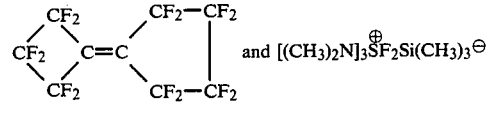 | 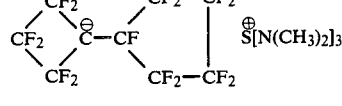 and 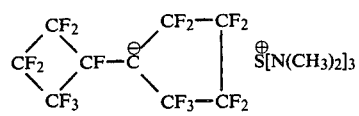 |

The carbanion salts of the invention are useful as intermediates in the synthesis of fluorine-containing compounds. They show a high anion reactivity, and readily displace halogens (Cl, Br, I) or sulfonates groups (—$OSO_2F$, —$OSO_2CF_3$, —$OSO_2Ar$) from organic compounds to form new fluorine-containing organic compounds. They can also be reacted with halogens ($I_2$, $Br_2$, $Cl_2$) to form the corresponding perfluoroalkyl halides. Many of the compounds that can be prepared from these carbanions are useful as solvents, dielectric liquids, radio-opaque diagnostic aids, drugs, and oxygen-carrying liquids for use in preparing artificial blood.

The carbanion salts of the invention are useful, per se, in the isomerization of fluoroolefins, as demonstrated by Utility Example O. The isolable tertiary carbanion salts of the invention also have utility as polymerization catalysts, for example, in polymerization reactions of the group transfer polymerization type disclosed: (1) by Webster et al. in *J. Am. Chem. Soc.*, 105 5706 (1983); and (2) in U.S. Pat. Nos. 4,414,372; 4,417,034; 4,508,880; and 4,524,196, wherein such processes one or more selected α,β-unsaturated compounds are contacted under polymerizing conditions with a selected silicon-, germanium- or tin-containing initiator and a selected Lewis acid or anion catalyst. More specific details may be found in the patents, the disclosures of which are hereby incorporated by reference. Utility Example M herein demonstrates such utility.

The following list of compounds demonstrates the variety of fluoro-organic compounds which can be prepared from the carbanion salts of the invention:

(1) 2-Bromo-1,1,1,3,3,4,4,5,5,5-decafluoro-2-(trifluoromethyl)pentane (Utility Example C) and 2-bromo-1,1,1,3,4,4,4-heptafluoro-2,3-bis(trifluoromethyl)butane (Utility Example K), are compounds which are useful as radio-opaque agents for contrast enhancement of x-rays.

(2) Bromononafluorocyclopentane (Utility Example L) is useful as a fire-extinguishing agent.

(3) Hexafluoropropylene trimers (Utility Example N) are useful as inert solvents of low dielectric constant.

The carbanion salts of the invention, in contrast to those known in the art, are readily soluble in organic solvents, are stable, and undergo a variety of reactions with electrophiles to give new fluoro-organic compounds. The tertiary salts are isolable as crystalline solids, are stable at elevated temperatures, and can be fully characterized by NMR spectroscopy.

In the following examples, temperatures are in degrees Celsius; $^1$NMR spectroscopic data are recorded in ppm downfield from tetramethylsilane standard; and $^{19}$F NMR spectroscopic data are recorded in ppm downfield from Freon ®-11 internal standard. All reactants are known compounds which are commonly available. In Examples 1 to 6, fluorotrimethylsilane is produced as a by-product.

EXAMPLE 1

Tris(dimethylamino)sulfonium
1,1,1,3,3,3-Hexafluoro-2-(trifluoromethyl)-2-propanide Octafluoroisobutylene, 14.8 g (0.074 mol), was slowly distilled into a stirred solution of 20.3 g (0.074 mol) of tris(dimethylamino)sulfonium difluorotrimethylsilicate in 75 mL of dry acetonitrile cooled to 0°. The reaction mixture was warmed to 25° and then evaporated to dryness under reduced pressure to give 24.4 g (86%) of tris(dimethylamino)sulfonium 1,1,1,3,3,3-hexafluoro-2-(trifluoromethyl)-2-propanide as a white solid: m.p. 160°-164°; $^{19}$F NMR (CD$_3$CN) −45.0 ppm; $^1$H NMR (CD$_3$CN) 2.88 ppm. Anal. Calcd. for C$_{10}$H$_{18}$F$_9$N$_3$S: C, 31.33; N, 10.96. Found: C, 31.89; N, 11.05.

EXAMPLE 2

Tris(piperidino)sulfonium
1,1,1,3,3,3-Hexafluoro-2-(trifluoromethyl)-2-propenide Octafluoroisobutylene, 8.34 g (0.042 mol), was slowly distilled into a stirred solution of 15.0 g (0.038 mol) of tris(piperidino)sulfonium difluorotrimethylsilicate in 50 mL of acetonitrile cooled to −10°. The reaction mixture was warmed to 25° and then evaporated to dryness under reduced pressure. The residue was washed with dry ether and then dried to give 17.3 g (90%) of tris(piperidino)sulfonium 1,1,1,3,3,3-hexafluoro-2-(trifluoromethyl)-2-propenide as white crystals: mp 138°-142°; $^1$H NMR (CD$_3$CN) δ 1.64 ppm (m, 18H), 3.21 ppm (m, 12H); $^{19}$F NMR (CD$_3$CN) δ −42.5 ppm (s). Anal. Calcd. for C$_{19}$H$_{30}$F$_9$N$_3$S: C, 45.32; H, 6.01. Found: C, 45.48; H, 6.17.

EXAMPLE 3

Tris(dimethylamino)sulfonium
1,1,1,3,3,4,4,5,5,5-Decafluoro-2-(trifluoromethyl)-2-pentanide 1,1,1,3,4,4,5,5,5-Nonafluoro-2-trifluoromethyl-2-pentene (26.4 g, 0.088 mol) was added to a solution of 22.0 g (0.08 mol) of tris(dimethylamino)sulfonium difluorotrimethylsilicate in 10 mL of acetonitrile. The reaction mixture was stirred until it was homogeneous, and then evaporated to dryness under reduced pressure to give 36.0 g (94%) of tris(dimethylamino)sulfonium 1,1,1,3,3,4,4,5,5,5-decafluoro-2-(trifluoromethyl)-2-pentanide; mp 60°-70°; $^{19}$F NMR (CD$_3$CN) δ −41.1 ppm (t,t, J=19.4, 6.4 Hz, 6F), −80.2 ppm (t, J=10.4 Hz, 3F), −91.7 ppm (well resolved multiplet, 2F), −125.3 ppm (m, 2F); $^1$H NMR (CD$_3$CN) δ 2.98 ppm (s), Anal. Calcd. for C$_{12}$H$_{18}$F$_{13}$N$_3$S: C, 29.82; H, 3.75; F, 51.10; N, 8.69. Found: C, 29.43; H, 3.87; F, 50.70; N, 8.77.

EXAMPLE 4

Tris(dimethylamino)sulfonium
1,1,1,3,4,4,4-Heptafluoro-2,3-bis(trifluoromethyl)-2-butanide A solution of tris(dimethylamino)sulfonium 1,1,1,3,4,4,4-heptafluoro-2,3-bis(trifluoromethyl)-2-butanide in acetonitrile was prepared by dissolving 8.00 g (0.027 mol) of tetrakis(trifluoromethyl)ethylene in a solution of 7.40 g (0.027 mol) of tris(dimethylamino)sulfonium difluorotrimethylsilicate in 30 mL of acetonitrile. The reaction was also repeated, using CD$_3$CN and propionitrile as solvents, to give solutions of the product in these solvents. $^{19}$F NMR (propionitrile, −79.7°) δ −39.1 ppm (m, 6F), −71.5 ppm (m, 6F) [the signal for the tertiary fluorine was too broad to be accurately measured]; $^{19}$F NMR (CD$_3$CN, 25°) δ −58.1 ppm (½w=27 Hz) [all fluorines equivalent due to rapid exchange at this temperature].

EXAMPLE 5

Tris(dimethylamino)sulfonium,
1,2,2,3,3,4,4,5,5-Nonafluorocyclopentanide

A solution of tris(dimethylamino)sulfonium 1,2,2,3,3,4,4,5,5-nonafluorocyclopentanide in acetonitrile was prepared by adding 15 g (0.071 mol) of perfluorocyclopentene to 21.4 g (0.078 mol) of tris(dimethylamino)sulfonium difluorotrimethylsilicate in 100 mL of acetonitrile cooled to 0°. Solutions of the pentanide were also prepared in propionitrile and benzonitrile by a similar procedure. $^{19}$F NMR (propionitrile) δ −79.4 ppm (m, 4F), −126.7 ppm (m, 4F) and −131.9 ppm (m, 1F).

EXAMPLE 6

Tris(dimethylamino)sulfonium
1-Perfluorocyclobutyl-1-perfluorocyclobutanide

A mixture of perfluorobicyclobutylene and perfluoro(1-cyclobutylcyclobutene) (2.0 g, 0.0062 mol) was added dropwise to a solution of 1.67 g (0.0061 mol) of tris(dimethylamino)sulfonium difluorotrimethylsilicate in 20 mL of acetonitrile at 0°. The reaction mixture was warmed to 25°, and then evaporated to dryness under reduced pressure to give the carbanion salt as a colorless viscous liquid: $^1$H NMR (CD$_3$CN) δ 2.85 ppm (s); $^{19}$F NMR (CD$_3$CN) δ −86.3 ppm (d, J=43 Hz, 4F atoms adjacent to anionic center), −156.2 ppm (broad, tertiary C–F), and 122–134 ppm (8F, unassigned).

Following are examples which demonstrate the utility of the compounds of the invention.

EXAMPLE A

2-Bromo-1,1,1,3,3,3-hexafluoro-2-(trifluoromethyl)propane

Bromine, 17.25 g (0.108 mol), was added dropwise at 0° to a solution of tris(dimethylamino)sulfonium 1,1,1,3,3,3-hexafluoro-2-(trifluoromethyl)-2-propanide, prepared by dissolving 33.4 g (0.12 mol) of tris(dimethylamino)sulfonium difluorotrimethylsilicate and 24.0 g (0.12 mol) of perfluoroisobutylene in 75 mL of benzonitrile, then pumping out the by-product fluorotrimethylsilane at reduced pressure. The reaction mixture was evacuated to transfer the volatile reaction product into a cold trap (−78°). Sublimation of the contents of the trap at atmospheric pressure gave 26.11 g (81%) of 2-bromo-1,1,1,3,3,3-hexafluoro-2-(trifluoromethyl)propane as a very volatile solid: m.p. (sublimation) 49°–51°; $^{19}F$ NMR (CDCl$_3$) δ −67.6 ppm (s).

EXAMPLE B 3,3,3-Trifluoro-2,2-bis(trifluoromethyl)propylbenzene

Benzyl bromide, 18.8 g (0.11 mol), was added dropwise at 10° to a solution of tris(dimethylamino)sulfonium 1,1,1,3,3,3-hexafluoro-2-(trifluoromethyl)-2-propanide, prepared by dissolving 24.4 g (0.122 mol) of octafluoroisobutylene and 33.6 g (0.122 mol) of tris(dimethylamino)sulfonium difluorotrimethylsilicate in 75 mL of acetonitrile. The reaction mixture was warmed to 25°, stirred overnight, and then poured into ice water. The aqueous mixture was extracted with ether, and the ether extracts were washed three times with water, dried (MgSO$_4$), and distilled to give 27.35 g (81%) of 3,3,3-trifluoro-2,2-bis(trifluoromethyl)propylbenzene as a colorless liquid, b.p. 53°–54° (12 mm), that solidified on cooling to a white solid: m.p. 32°–33°; $^1H$ NMR (CDCl$_3$) δ 3.39 ppm (s, 2H), 7.28 ppm (s, 5H); $^{19}F$ NMR (CDCl$_3$) δ −62.3 ppm (s). Anal. Calcd. for C$_{11}$H$_7$F$_9$: C, 42.59; H, 2.28; F, 55.13. Found: C, 42.45; H, 2.23; F, 55.00.

EXAMPLE C

2-Bromo-1,1,1,3,3,4,4,5,5,5-decafluoro-2-(trifluoromethyl)pentane

Bromine, 7.99 g (0.05 mol), was added dropwise at 0° to a solution of 0.05 mol of tris(dimethylamino)sulfonium 1,1,1,3,3,4,4,5,5,5-decafluoro-2-(trifluoromethyl)-2-pentanide, prepared as in Example D (except for the amounts), in 40 mL of benzonitrile. The reaction mixture was warmed to 25°, and the volatile portion was distilled out under reduced pressure, and then redistilled at atmospheric pressure to give 12.8 g (75%) of 2-bromo-1,1,1,3,3,4,4,5,5,5-decafluoro-2-(trifluoromethyl)-pentane as a colorless liquid: b.p. 96.5°–97.2°; $^{19}F$ NMR (CDCl$_3$) δ −65.2 ppm (m, 6F), −81.1 ppm (t, 3F), −105.9 ppm (2F) and −122.6 ppm (2F). Anal. Calcd. for C$_6$BrF$_{13}$: C, 18.06; F, 61.91. Found: C, 17.90; F, 61.55.

EXAMPLE D

2-Chloro-1,1,1,3,3,4,4,5,5,5-decafluoro-2-(trifluoromethyl)pentane

Chlorine, 4.73 g (0.067 mol), was slowly distilled into a solution of tris(dimethylamino)sulfonium 1,1,1,3,3,4,4,5,5,5-decafluoro-2-(trifluoromethyl)-2-pentanide, cooled to 0°, prepared by dissolving 20.2 g (0.073 mol) of tris(dimethylamino)sulfonium difluorotrimethylsilicate and 20.0 g (0.0665 mol) of 1,1,1,3,4,4,5,5,5-nonafluoro-2-trifluoromethyl-2-pentene in 75 mL of benzonitrile, then pumping out the by-product fluorotrimethylsilane at reduced pressure. The reaction mixture was warmed to 25°, and then the most volatile portion was distilled out at reduced pressure and then redistilled at atmospheric pressure to give 18.2 g (77%) of the desired chloro compound as a colorless liquid: b.p. 84°–85°; $^{19}F$ NMR (CDCl$_3$) δ −67.7 ppm (t,t, J=12, 10 Hz, 6F), −81.1 ppm (t, J=13 Hz, 3F), −109.4 ppm (m, 2F) and −123.5 ppm (m, 2F). Anal. Calcd. for C$_6$ClF$_{13}$: C, 20.33. Found: C, 19.55.

EXAMPLE E 3,3,4,4,5,5,5-Heptafluoro-2,2-bis(trifluoromethyl)pentane

Methyl fluorosulfate (7.6 g, 0.0665 mol) was added dropwise at 0° to a stirred solution of tris(dimethylamino)sulfonium 1,1,1,3,3,4,4,5,5,5-decafluoro-2-(trifluoromethyl)-2-pentanide, prepared by dissolving 20.2 g (0.073 mol) of tris(dimethylamino)sulfonium difluorotrimethylsilicate and 20.0 g (0.0665 mol) of 1,1,1,3,4,4,5,5,5-nonafluoro-2-trifluoromethyl-2-pentene in 75 mL of benzonitrile. The reaction mixture was warmed at 25°, and the most volatile portion of the reaction mixture was distilled out under reduced pressure. The distillate was redistilled at atmospheric pressure to give 13.27 g (60%) of 3,3,4,4,5,5,5-heptafluoro-2,2-bis(trifluoromethyl)pentane as a colorless liquid: b.p. 88°–89°; $^{19}F$ NMR (CCl$_3$F) δ −67.7 ppm (t,t, 6F), −81.1 ppm (t, 3F), −110.5 ppm (m, 2F) and −123.7 ppm (m, 2F); $^1H$ NMR (CCl$_3$F) δ1.72 ppm. Anal. Calcd. for C$_7$H$_3$F$_{13}$: C, 25.17; H, 0.91; F, 73.93. Found: C, 24.88; H, 0.87; F, 73.64.

EXAMPLE F 4,4,5,5,6,6,6-Heptafluoro-3,3-bis(trifluoromethyl)hexane

The procedure described for Example E was repeated except that the methyl fluorosulfate was replaced with 10.28 g (0.067 mol) of diethyl sulfate. 4,4,5,5,6,6,6-Heptafluoro-3,3-bis(trifluoromethyl)hexane was obtained as a colorless liquid: b.p. 104°; $^{19}F$ NMR (CDCl$_3$) δ −64.1 ppm (t,t, 6F), −80.5 ppm (t, 3F), −107.1 ppm (m, 2F) and −122.6 ppm (2F); $^1H$ NMR (CDCl$_3$) δ 1.24 ppm (t, J=7 Hz, 3H) and 2.32 ppm (q, J=7 Hz, 2H). Anal. Calcd. for C$_8$H$_5$F$_{13}$: C, 27.60; H, 1.45; F, 70.95. Found: C, 27.99; H, 1.68; F, 70.61.

EXAMPLE G 3,3,4,4,5,5,5-Heptafluoro-2,2-bis(trifluoromethyl)pentylbenzene

Benzyl bromide, 4.77 g (0.028 mol), was added dropwise to a solution of 15.0 g (0.031 mol) of tris(dimethylamino)sulfonium 1,1,1,3,3,4,4,5,5,5-decafluoro-2-(trifluoromethyl)-2-pentanide in 50 mL of acetonitrile at 25°, and the reaction mixture was stirred overnight and then poured into water. The aqueous mixture was extracted with ether, and the ether extracts were dried (MgSO$_4$) and then distilled to give 7.5 g (66%) of 3,3,4,4,5,5,5-heptafluoro-2,2-bis(trifluoromethyl)pentylbenzene as a colorless liquid: b.p. 62°–63° (5 mm); $^{19}F$ NMR (CDCl$_3$) δ −62.7 ppm (t,t 6F), −80.7 ppm (t, 3F), −106.3 ppm (m, 2F) and −123.3 ppm (2F); $^1$H NMR (CDCl$_3$) δ 3.52 ppm (s, 2H) and 7.27 ppm (s, 5H). Anal. Calcd. for C$_{13}$H$_7$F$_{13}$: C, 38.07; H, 1.72; F, 60.21. Found: C, 37.82; H, 1.73; F, 60.42.

EXAMPLE H

4-Nitro-2',2',3',3',4',4',4'-heptafluoro-1',1'-bis(trifluoromethyl)benzeneazobutane p-Nitrobenzenediazonium hexafluorophosphate, 33.6 g (0.11 mol), was added portionwise at 0° to a solution of tris(dimethylamino)sulfonium 1,1,1,3,3,4,4,5,5,5-decafluoro-2-(trifluoromethyl)-2-pentanide, prepared by dissolving 31.33 g (0.11 mol) of tris(dimethylamino)sulfonium difluorotrimethylsilicate and 34.2 g (0.11 mol) of 1,1,1,3,4,4,5,5,5-nonafluoro-2-trifluoromethyl-2-pentene in 75 mL of acetonitrile. The reaction mixture was warmed to 25°, stirred for 1.5 h, and then poured into 800 mL of ice water. The water was decanted from the semi-solid residue, and the residue was washed with ether to give 24.5 g (72%) of tris(dimethylaminosulfonium)hexafluorophosphate, m.p. 257°–260°. The ether wash was extracted 3× with water, dried (MgSO$_4$), and evaporated to dryness to give 45.8 g (89%) of the azo compound as a bright orange oil: n$_D$25 1.4292; $^{19}$F NMR (CDCl$_3$) δ −63.8 ppm (m, 76F), −80.9 ppm (t, 3F), −110.5 ppm (m, 2F) and −124.2 ppm (m, 2F); $^1$H NMR (CDCl$_3$) δ 8.3 ppm (A$_2$B$_2$ pattern). Anal. Calcd. for C$_{12}$H$_4$F$_{13}$N$_3$O$_2$: C, 30.72; H, 0.86; F, 52.64; N, 8.96. Found: C, 30.84. H, 0.87; F, 52.51; N, 8.89.

EXAMPLE I

2',2',3',3',4',4',4'-Heptafluoro-1',1'-bis(trifluoromethyl)benzeneazobutane

The procedure described in Example H was repeated, except that an equivalent amount of benzenediazonium hexafluorophosphate was used in place of the p-nitrobenzenediazonium hexafluoro phosphate. There was obtained a 72% yield of the azo compound as an orange oil: n$_D$25 1.3985; $^{19}$F NMR (CDCl$_3$) δ −64.0 ppm (6F), −81.0 ppm (t, 3F), −110.6 ppm (m, 2F) and −124.0 ppm (m, 2F); $^1$H NMR (CDCl$_3$) δ 7.5 ppm (m, 3H), 7.85 ppm (m, 2H). Anal. Calcd. for C$_{12}$H$_5$F$_{13}$N$_2$: C, 33.98; H, 1.19; F, 58.22; N, 6.61. Found: C, 34.15; H, 1.21; F, 58.22; N, 6.61.

EXAMPLE J 1,1,1,3,3,4,4,5,5,5-Decafluoro-2-nitroso-2-(trifluoromethyl)pentane Nitrosyl chloride, 5.10 g (0.078 mol), was slowly distilled into a solution of tris(dimethylamino)sulfonium 1,1,1,3,3,4,4,5,5,5-decafluoro-2-(trifluoromethyl)-2-pentanide, cooled to 0°, prepared by dissolving 23.8 g (0.086 mol) of tris(dimethylamino)sulfonium difluorotrimethylsilicate and 21.5 g (0.0717 mol) of 1,1,1,3,4,4,5,5,5-nonafluoro-2-trifluoromethyl-2-pentene in 100 mL of acetonitrile. The lower blue layer of the reaction mixture was separated, washed with water, dried (MgSO$_4$) and distilled to give the nitroso compound as a deep blue liquid: b.p. 72°–74°; $^{19}$F NMR (CDCl$_3$) δ −63.5 ppm (m, 6F), −81.0 ppm (t, 3F), −109.7 ppm (m, 2F) and −124.7 ppm (m, 2F); IR (neat) 1620 cm$^{-1}$. Anal. Calcd. for C$_6$F$_{13}$NO; C, 20.65; N, 4.01. Found: C, 20.41; N, 4.29.

EXAMPLE K

2-Bromo-1,1,1,3,4,4,4-heptafluoro-2,3-bis(trifluoromethyl)butane

Bromine, 4.0 g (0.025 mol) was added dropwise to a solution of tris(dimethylamino)sulfonium 1,1,1,3,4,4,4-heptafluoro-2,3-bis(trifluoromethyl)-2-butanide, cooled to 0°, prepared by dissolving 6.9 g (0.025 mol) of tris(dimethylamino)sulfonium difluorotrimethylsilicate and 6.3 g (0.021 mol) of tetrakis(trifluoromethyl)ethylene in 25 mL of benzonitrile, then pumping out the by-product fluorotrimethylsilane at reduced pressure. The product was distilled out of the reaction mixture at reduced pressure, and then redistilled at atmospheric pressure to give the bromide as a colorless liquid: b.p. 92°–93°; $^{19}$F NMR (CDCl$_3$) δ −63.5 ppm (septet, d, J=10, 5 Hz, 6F) and −160.7 ppm (m, 1F). Anal. Calcd. for C$_6$BrF$_{13}$: C, 18.06; Br, 20.03; F, 61.91. Found: C, 18.14; Br, 19.88; F, 61.76.

EXAMPLE L

Bromononafluorocyclopentane

Bromine was added to a solution of tris(dimethylamino)sulfonium 1,2,2,3,3,4,4,5,5-nonafluorocyclopentanide in benzonitrile, prepared as described in Example 5. Distillation of the reaction mixture gave bromononafluorocyclopentane as a colorless liquid: b.p. 64°–65°; $^{19}$F NMR (CCl$_3$F) δ −112.4 ppm (d, J=262 Hz, 2F), −136.2 ppm (d, J=262 Hz, 2F), −141.4 ppm (m, 1F), −125.4 ppm (d, J=255 Hz, 2F) and −127.8 ppm (d, J=255 Hz, 2F).

EXAMPLE M

Polymerization of Methyl Methacrylate with Tris(dimethylamino)sulfonium 1,1,1,3,3,3-Hexafluoro-2-(trifluoromethyl)-2-propanide A solution of 60 mg of tris(dimethylamino)sulfonium 1,1,1,3,3,3-hexafluoro-2-(trifluoromethyl)-2-propanide in 0.25 mL of acetonitrile was added to a solution of 0.60 g of methyl trimethylsilyl dimethyl ketene acetal in 25 mL of tetrahydrofuran at −78°. Methyl methacrylate, 5.0 mL, was added, and the reaction mixture was warmed to 0° at which temperature an exothermic rection ensued and the temperature rose to 45°. After cooling to 25°, another 5.0 mL of methyl methacrylate was added. After the exotherm subsided, another 5.0 mL of methyl methacrylate was added. Evaporation of the volatile portion gave 13.6 g of colorless polymer. Gel permeation chromatographic analysis showed $\overline{M}_w$ of 3920, $\overline{M}_n$ of 3030.

EXAMPLE N

Trimerization of Hexafluoropropene

This example illustrates the utility of a carbanion salt of the invention in the trimerization of a fluoroolefin. The following equations depict the formation of the carbanion salt in the first step, followed by reaction of the carbanion salt with excess olefin to produce trimers. The by-products are not shown in the equations.

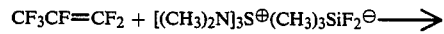

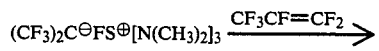

-continued

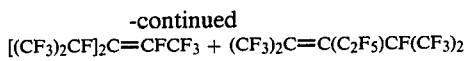

Hexafluoropropene was passed into a melting ice-cooled flask that had been evacuated and contained a solution of 5.0 g of tris(dimethylamino)sulfonium difluorotrimethylsilicate in 100 mL of benzonitrile. Hexafluoropropene pressure of 700 mm of Hg was maintained for about 7 h. The lower organic layer was separated and distilled to give 600.0 g of hexafluoropropene trimers as a colorless liquid, bp 113°–113.6°. $^{19}$F NMR analysis indicated that two principal components of the trimer mixture were perfluoro(2,4-dimethyl-3-ethyl-2-pentene), 57%, and perfluoro(4-methyl-3-isopropyl-2-pentene), 37%.

EXAMPLE O

Isomerization of Perfluoro-1-heptene to Trans-Perfluoro-3-heptene

This example illustrates the utility of a carbanion salt of the invention in the isomerization of a fluoroolefin. The following equations, wherein TASF is tris(dimethylamino)sulfonium difluorotrimethylsilicate, depict the steps involved in the isomerization; carbanion salts of the invention are formed as intermediates.

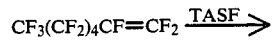 (1)

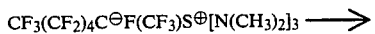

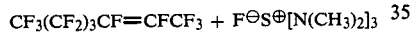

 (2)

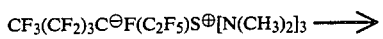

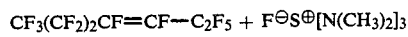

A mixture of 2.53 g (9.2 mmol) of tris(dimethylamino)sulfonium difluorotrimethylsilicate (TASF), 1.60 g (4.6 mmol) of perfluoro-1-heptene, and 3 mL of dry benzonitrile was stirred and warmed to 40°. The lower organic layer was separated and washed with water to give trans-perfluoro-3-heptene as a colorless liquid: $^{19}$F NMR (CCl$_3$F) $\delta$ −81.7 ppm (m, 3F), −118.3 ppm (m, 2F), −123.3 ppm (m, 2F), −124.1 ppm (m, 2F), −126.6 ppm (m, 2F), −89.3 ppm (d,d,t, J=41, 52, 6 Hz, 1F), −105.8 ppm (d,d,t,t, J=117, 52, 28, 3, 1F), and −189.4 ppm (d,d,m, J=117, 41 Hz, 1F).

BEST MODE FOR CARRYING OUT THE INVENTION

The best mode presently contemplated is represented by Examples 1–3 and 8, especially Examples 1 and 3.

INDUSTRIAL APPLICABILITY

The carbanion salts of the invention are intermediates in the preparation of fluorinated compounds which find commercial applications in, for example, industrial solvents, dielectric and hydraulic fluids, pharmaceutical products, radio-opaque diagnostic aids, oxygen-carrying liquids for use in artificial blood preparation, and as catalysts in the polymerization of $\alpha,\beta$-unsaturated compounds such as (meth)acrylate esters, polymers from which find well-known industrial uses.

Although the preferred embodiments of the invention have been illustrated and described, it is to be understood that there is no intent to limit the invention to the precise constructions herein disclosed, and the right is reserved to all changes and modifications coming within the scope of the invention as defined in the appended claims.

I claim:

1. In a group transfer polymerization process of monomer in the presence of a suitable silicon-, germanium- or tin-containing initiator and a catalyst, said process characterized in that the catalyst is the tris(disubstituted amino)sulfonium perfluorocarbanion salt of the formula

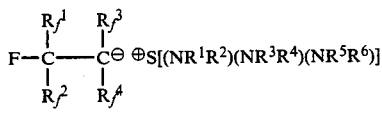

wherein
R$^1$ through R$^6$, each selected independently, are C$_1$–C$_{20}$ alkyl, each having at least 2 alpha hydrogen atoms, or any or all of the pairs R$^1$ and R$^2$, R$^3$ and R$^4$, and R$^5$ and R$^6$, each pair selected independently, are —CH$_2$—$_4$ or —CH$_2$—$_2$CHY—CH$_2$—$_2$, wherein Y is hydrogen or methyl;

R$_f^1$, R$_f^2$ and R$_f^3$, each selected independently, are F, C$_{1-20}$ perfluoroalkyl or C$_{4-12}$ perfluorocycloalkyl; and R$_f^4$ is C$_{1-20}$ perfluoroalkyl or C$_{4-12}$ perfluorocycloalkyl; or any one of the pairs R$_f^1$ and R$_f^2$, R$_f^3$ and R$_f^4$, R$_f^1$ and R$_f^3$, and R$_f^2$ and R$_f^4$, taken together, is —CF$_2$—$_n$ wherein n is an integer and is 2 to 6; or each of the pairs R$_f^1$ and R$_f^2$ and R$_f^3$ and R$_f^4$, or each of the pairs R$_f^1$ and R$_f^3$ and R$_f^2$ and R$_f^4$, taken together, is —CF$_2$—$_n$ wherein n, each selected independently, is an integer and is 2 to 6.

2. Process of claim 1 wherein R$_f^1$ is F, R$_f^2$ is C$_{1-10}$ perfluoroalkyl and each of R$_f^3$ and R$_f^4$ is CF$_3$.

3. Process of claim 2 wherein each of R$^1$–R$^6$ is CH$_3$.

4. Process of claim 3 wherein R$_f^2$ is CF$_3$ or C$_2$F$_5$.

5. Process of claim 1 wherein each of R$_f^1$ and R$_f^2$ is F and each of R$_f^3$ and R$_f^4$ is CF$_3$.

6. Process of claim 5 wherein each of R$^1$–R$^6$ is CH$_3$.

7. Process of claim 6 wherein the monomer is methyl methacrylate.

* * * * *

UNITED STATES PATENT AND TRADEMARK OFFICE
CERTIFICATE OF CORRECTION

PATENT NO. : 4,621,126
DATED : November 4, 1986
INVENTOR(S) : William Joseph Middleton It is certified that error appears in the above—identified patent and that said Letters Patent is hereby corrected as shown below:

Column 2, line 11, " $-CH_2-_4$ " should be -- $(CH_2)_4$ --;
" $-CH_2-_2$ " should be -- $(CH_2)_2$ --.

Column 2, lines 19 and 23, " $-CF_2-_n$ " should be -- $(CF_2)_n$ --.

Column 3, line 61, " $-CH_2-_5$ " should be -- $(CH_2)_5$ --.

Column 4, line 2, " $-CH_2-_5$ " should be -- $(CH_2)_5$ --.

Column 4, line 64, there should be a comma and space after "105".

Claim 1, line 38, " $-CH_2-_4$ " should be -- $(CH_2)_4$ -- and
" $-CH_2-_2$ " should be -- $(CH_2)_2$ --.

Claim 1, line 45, " $-CF_2-_n$ " should be -- $(CF_2)_n$ --.

Claim 1, line 49, " $-CF_2-_n$ " should be -- $(CF_2)_n$ --.

Signed and Sealed this

Thirty-first Day of March, 1987

*Attest:*

DONALD J. QUIGG

*Attesting Officer*  *Commissioner of Patents and Trademarks*